(12) United States Patent
Farrerons Gallemi et al.

(10) Patent No.: US 6,916,828 B2
(45) Date of Patent: Jul. 12, 2005

(54) CARBAMATES DERIVATIVED FROM ARYLAKYLAMINES

(75) Inventors: Carles Farrerons Gallemi, Mataro (ES); Juan Lorenzo Catena Ruiz, L'Hospitalet de Llobregat (ES); Anna Fernandez Serrat, Sant Cugat del Valles (ES); Ignacio José Miquel Bono, L'Hospitalet de Llobregat (ES); Dolors Balsa Lopez, Badalona (ES); José Ignacio Bonilla Navarro, Daganzo de Arriba (ES); Carmen Lagunas Arnal, L'Hospitalet de Llobregat (ES); Carolina Salcedo Roca, Corbera (ES); Andrés Fernandez Garcia, Barcelona (ES)

(73) Assignee: Laboratorios S.A.L.V.A.T., S.A., Esplugues de Llobregat (ES)

( * ) Notice: Subject to any disclaimer, the term of this patent is extended or adjusted under 35 U.S.C. 154(b) by 0 days.

(21) Appl. No.: 10/312,227
(22) PCT Filed: Jun. 25, 2001
(86) PCT No.: PCT/ES01/00252
 § 371 (c)(1),
 (2), (4) Date: Jul. 28, 2003
(87) PCT Pub. No.: WO02/00652
 PCT Pub. Date: Jan. 3, 2002

(65) Prior Publication Data
US 2004/0063950 A1 Apr. 1, 2004

(30) Foreign Application Priority Data
Jun. 27, 2000 (ES) .......................................... 200001661

(51) Int. Cl.$^7$ ..................... A61K 31/439; C07D 453/02; A61P 13/10
(52) U.S. Cl. ...................... 514/305; 546/137; 546/133; 546/135
(58) Field of Search ................. 546/137, 133, 546/135; 514/305

(56) References Cited

U.S. PATENT DOCUMENTS 3,287,471 A    11/1966  Cusic et al.

FOREIGN PATENT DOCUMENTS

| EP | 747355 | 12/1996 |
| EP | 801067 | 11/1997 |
| JP | 04095071 | 3/1992 |
| WO | WO 02/051841 | * 7/2002 |

OTHER PUBLICATIONS van Zwieten et al. Cardiovascular Durgs and Therapy. 1995, 9(1); 159–67.*
Xu et al. Chemical & Pharmaceutical Bulletin, 1998, 46(2); 231–41.*

* cited by examiner

*Primary Examiner*—Evelyn Mei Huang
(74) *Attorney, Agent, or Firm*—Merchant & Gould P.C.

(57) ABSTRACT

The invention relates to carbamates having general structure (I), wherein: R1, R2 and R3 are H, OH, SH, CN, F, Cl, Br, I, ($C_1$–$C_4$)-alkylthio, ($C_1$–$C_4$)-alkoxyl, ($C_1$–$C_4$)-alkoxyl substituted by one or several F radicals, carbamoylamine, ($C_1$–$C_4$)-alkyl and ($C_1$–$C_4$)-alkyl substituted by one or several F or OH radicals; R4 represents a substituted or non-substituted cycloalkyl or cycloaryl radical (a heteroalkyl radical or not). The amine of the quinuclidine ring can also be forming quatemary ammonium salts or in an oxidized state (N-oxide). Carbamates (I) are antagonists of the $M_3$ muscarinic receptor, and selectively, the $M_2$ receptor. Hence, they can be used in the treatment of urinary incontinence (particularly due to bladder instability), irritable bowel syndrome, diseases of the respiratory tract (particularly chronic obstructive pulmonary disease, chronic bronchitis, asthma, emphysema and rhinitis) and in ophthalmologic operations.

10 Claims, No Drawings

CARBAMATES DERIVATIVED FROM ARYLAKYLAMINES

This application is a §371 application of PCT/ES01/00252, filed on Jul. 25, 2001, which claims benefit of Spanish App. No. P200001661, filed on Jun. 27, 2000.

The present invention relates to new compounds of type quinuclidyl N-phenyl-N-alkyl carbamate acting as muscarinic receptor antagonists, to the preparation of such compounds, and to the use of the same in the prevention and treatment of diseases related with respiratory tract, digestive tract, and urinary system.

BACKGROUND OF THE ART

It is known that compounds having a muscarinic receptor antagonizing effect induce bronchodilation, gastrointestinal motility inhibition, gastric acid secretion reduction, dry mouth, mydriasis, tachycardita, as well as urinary bladder contraction inhibition.

Between 1983 and 1993, continuous advances were produced in the knowledge of muscarinic receptor pharmacology. During this period, a total of five human genes codifying muscarinic-receptor subtypes (m1, m2, m3, m4 and m5) were cloned and expressed, which encoded five functional receptors ($M_1$, $M_2$, $M_3$, $M_4$ and $M_5$). Although $M_5$ is not completely characterized, it is already considered a functional receptor according to NC-IUPHAR *Guidelines* (M. P. Caulfield et al.; *Pharmacol. Rev.* 1998, 50, 279–290).

The $M_1$ receptor is a postsynaptic neuronal receptor mainly located in brain and peripheral parasympathetic glands. In smooth cardiac muscle there is a major population of $M_2$ receptors. The $M_3$ receptor is predominantly located in glandular exocrine tissues such as salivary glands. The $M_4$ receptor is mainly present in cerebral cortex, striatum and some peripheral locations in specific species. In the smooth muscle of intestinal tract, bladder and bronchus, $M_2$ and $M_3$ receptors coexist. Nevertheless, functional information commonly accepted indicates that the $M_3$ receptor is the responsible for the contractile effect of the endogenous neurotransmitter in the latter three tissues. Thus, it seems interesting to obtain $M_3$ receptor selective antagonists to avoid the adverse effects due to blockade of other muscarinic receptors. At present, oxybutynin (Nippon Shinyaku), and tolterodine (Pharmacia) among others are commercially available compounds, both showing reduced selectivity for $M_2$ and $M_3$ receptors. However, darifenacin (Pfizer), and YM-905 (Yamanouchi), both in development phase, exhibit $M_3$ antagonist activity without any significant affinity towards the $M_2$ receptor.

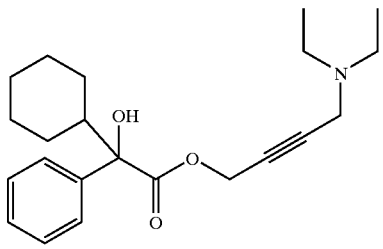

Oxybutynin

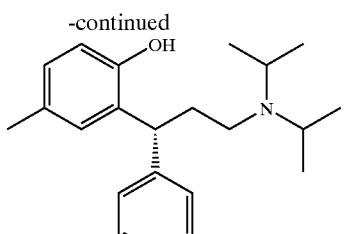

Tolterodine

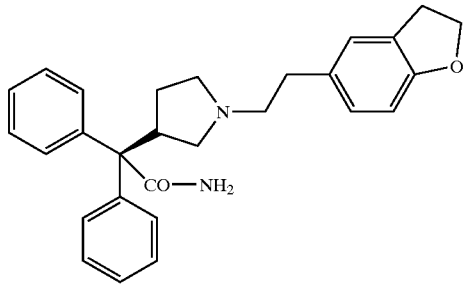

Darifenacin

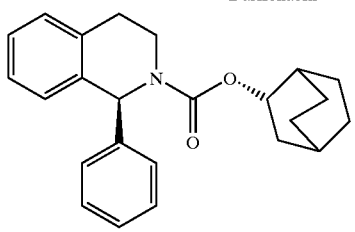

YM-905

The following are some patent applications claiming compounds with carbamic structures as selective $M_3$ receptor antagonists: JP 04/95071-A, WO 95/06635-A, EP 747355-A and EP 801067-A. All of them describe carbamates different to those described in the present invention, and the last one describes the structurally nearest to the hereby claimed.

Therefore, it is understood that there is a big interest in providing new therapeutic agents that are selective $M_3$ receptor antagonists.

SUMMARY OF THE INVENTION

An aspect of the present invention relates to the provision of new carbamates of general formula (I)

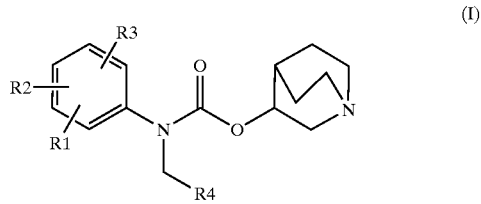

(I)

and stereoisomers, mixtures of stereoisomers, pharmaceutically acceptable salts, and pharmaceutically acceptable solvates thereof, wherein: R1, R2 and R3 are radicals independently selected from the group consisting of H, OH, SH, CN, F, Cl, Br, I, carbamoylamine, ($C_1$–$C_4$)-alkylthio, ($C_1$–$C_4$)-alkoxyl, ($C_1$–$C_4$)-alkoxyl substituted with one or several F, ($C_1$–$C_4$)-alkyl, and ($C_1$–$C_4$)-alkyl substituted with one or several F or OH; alternatively, either R1 and R2, or R2 and R3 may be forming a biradical selected from the group consisting of —$CH_2$—$CH_2$—$CH_2$—, and —$CH_2$—$CH_2$—$CH_2$—$CH_2$—.

In compounds of formula (I), R4 is a radical selected from the group consisting of cyclopropyl, cyclobutyl, cyclopentyl, cyclohexyl, cyclohexenyl, norbornenyl, bicyclo[2.2.1]heptanyl, 2-, 3-thienyl, 2-, 3-furyl, 2-, 3-, 4-pyridyl, 1-, 2-naphtyl, 1-, 2-benzodioxolanyl, 1-, 2-behzodioxanyl, phenyl, and phenyl substituted with one or several substituents selected from the group consisting of OH, SH, CN, F, Cl, Br, I, carbamoylamine, hydroxycarbonyl, ($C_1$–$C_4$)-alkoxycarbonyl, ($C_1$–$C_4$)-alkylthio, ($C_1$–$C_4$)-alkyl, ($C_1$–$C_4$)-alkoxyl, ($C_1$–$C_4$)-alkyl substituted with one or several F or OH, and ($C_1$–$C_4$)-alkoxyl substituted with one or several F.

In a particular embodiment, R4 is phenyl or phenyl substituted with one or several substituents selected from the group consisting of: OH, SH, CN, F, Cl, Br, I, carbamoylamine, hydroxycarbonyl, ($C_1$–$C_4$)-alkoxicarbonyl, ($C_1$–$C_4$)-alkylthio, ($C_1$–$C_4$)-alkyl, ($C_1$–$C_4$)-alkoxyl, ($C_1$–$C_4$)-alkyl substituted with one or several F or OH, and ($C_1$–$C_4$)-alkoxyl substituted with one or several F. In another particular embodiment, R4 is a radical selected from the group consisting of cyclopropyl, cyclobutyl, cyclopentyl, cyclohexyl, cyclohexenyl, norbornenyl, bicyclo[2.2.1]heptanyl, 2-, 3-thienyl, 2-, 3-furyl, 2-, 3-, 4-piridyl, 1-, 2-naphtyl, 1-, 2-benzodioxolanyl, and 1-, 2-benzodioxanyl.

The nitrogen atom of the quinuclidine ring can be in an oxidized state (N-oxide) or as a pharmaceutically acceptable quaternary alkylamonium salt, wherein the alkylic chain, from 1 to 4 carbon atoms, may be linear or branched.

Particularly preferred are compounds of formula (I) where the carbon 3 of the quinuclidine ring is (R), having the formula:

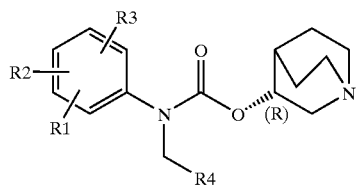

In cases where compounds of formula (I) have an asymmetric carbon, the racemic mixtures thereof can be resolved in their enantiomers by conventional methods, such as separation by chromatography with chiral stationary phase or by fractioned crystallization of their diastereoisomeric salts. The later can be prepared by reaction with enantiomerically pure acids. Chiral compounds of formula (I) may also be obtained by enantioselective synthesis through chiral precursors.

The present invention is also related to physiologically acceptable salts of carbamates of general structure (I), in particular to addition salts with mineral acids such as hydrochloric, hydrobromic, nitric, sulphuric, and phosphoric acids, as well as with organic acids such as oxalic, succinic, fumaric, tartaric and maleic acids.

The present invention is also related to N-oxides of carbamates of general structure (I) and to quaternary ($C_1$–$C_4$)-alkylamonium salts of such carbamates with pharmaceutically acceptable anions.

Compounds of general structure (I) can be prepared by two general methods (namely, A and B) represented in the scheme below. Starting arylalkylamines (II) are commercially available, or may be obtained by known methods such as alkylation of anilines, reductive amination, or reduction of anilides.

According to Method A, acylation of the arylalkylamine (II) through a chloroformate (e.g. methylchloroformate, ethylchloroformate or 4-nitrophenylchloroformate) in an inert solvent (e.g. dimethylformamide, $CH_2Cl_2$, 1,2-dichloroethane, tetrahydrofurane or toluene) is carried out first, at a temperature ranging from 0° C. to the reflux temperature of the solvent. In some cases, it is advisable to carry out the reaction using the corresponding chloroformate as solvent, or using a base such as a tertiary amine or potassic carbonate. Then, the alkoxylic moiety is introduced by a transesterification reaction between the carbamate intermediate (III) and 3-quinuclidol, using a base such as sodium metal, sodium hydride, or sodium methoxide. The reaction can be carried out at a temperature ranging from 20° C. to the reflux temperature of the used solvent.

According to Method B, 3-quinuclidol is first reacted with a chloroformate (e.g. trichloromethylchloroformate) in an inert solvent (e.g. dimethylformamide, $CH_2Cl_2$, 1,2-diclhoroethane) at the reflux temperature of the solvent in order to obtain the corresponding hydrochloride of quinuclidol chloroformate. Then, arylalkylamine (II) is acylated with quinuclidol chloroformate. The reaction is carried out in an inert solvent (e.g. dimethylformamide, $CH_2Cl_2$, $CHCl_3$, 1,2-dichloroethane) at a temperature ranging from 20° C. to the reflux temperature of the solvent.

As it is illustrated in the enclosed human muscarinic receptor binding tests, the compounds of the present invention are selective $M_3$ receptor antagonists versus $M_2$ receptor. For this reason they can be used for the treatment of urinary incontinence (particularly, the one caused by unstable bladder), irritable bowel syndrome, and respiratory disorders (particularly, chronic obstructive pulmonary disease, chronic bronchitis, asthma, emphysema, and rhinitis), as well as in ophthalmic interventions.

Thus, another aspect of the present invention is the use of carbamates of formula (I) for the preparation of medicaments for the treatment of the following diseases: urinary incontinence, particularly when it is caused by unstable bladder; irritable bowel syndrome; respiratory disorders, especially chronic obstructive pulmonary disease, chronic bronchitis, asthma, emphysema, and rhinitis. Furthermore, their use for the preparation of a medicament for ophthalmic interventions, is also forming part of this aspect of the invention.

Method A

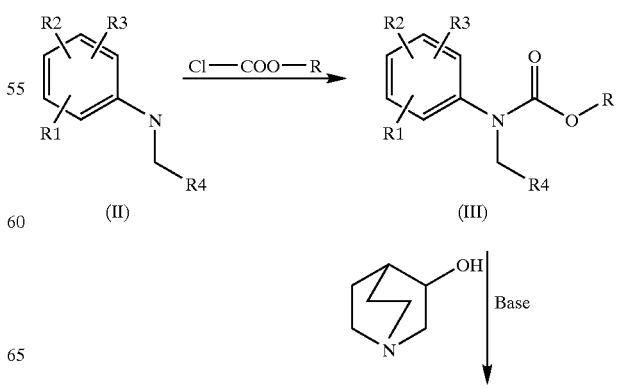

-continued

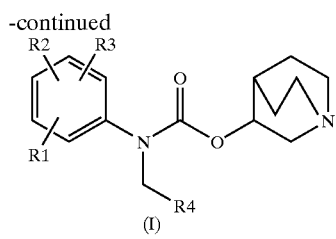

Method B

Cl—COO—R + HO—[quinuclidyl] → Cl—C(O)—O—[quinuclidyl·HCl]

[structure II with R1, R2, R4]

↓

(I)

Binding Test to Human $M_2$ and $M_3$ Muscarinic Receptors

The following tests show the $M_3$ antagonist activity of compounds of formula (I), as well as their selectivity towards the $M_2$ receptor. The results obtained for cloned human muscarinic $M_2$ and $M_3$ receptors are listed, and the used methodology is described.

Membranes from CHO-K1 cells transfected with human $M_2$ or $M_3$ receptors (Receptor Biology) were used. The summarised experimental procedure for both receptors was the following: membranes (15–20 µg) were incubated with [$^3$H]-NMS (0.3–0.5 nM) for 60 min at 25° C., in presence or absence of the antagonists. Incubation was carried out in 96 wells polystyrene microplates in a total incubation volume of 0.2 mL of PBS pH 7.4. Non specific binding was determined in parallel assays in presence of atropine (5 µM). Samples were filtered through type GF/C glass fibre, preincubated with PEI 0.3%. Filters were washed 3–4 times with 50 mM Tris-HCl, 0.9% NaCl, pH 7.4 at 4° C., and dried at 50° C. for 45 min. Filter bound radioactivity was quantified by liquid scintillation counting.

For the calculation of the inhibition constant ($K_i$), displacement curves were analysed by non-linear regression (GraphPad Prism). Dissociation constant ($K_D$) of [$^3$H]-NMS for each receptor was obtained through the saturation curves obtained in the same conditions as the experiments carried out with the antagonists. The results obtained, expressed as the mean of two independent experiments, each performed in duplicate, are shown in the table below. $M_2/M_3$ ratios greater than 1 indicates a $M_3$ selective antagonist activity.

The invention will be illustrated by the following non-limiting examples.

EXAMPLES

Intermediate 1

(R)-3-quinuclidyl chloroformate, hydrochloride

To a solution of 8.7 mL (74.8 mmol) of trichloromethyl chloroformate in 240 mL of dichloromethane, a solution of 4.75 g (37.4 mmol) of (R)-3-quinuclidol in 240 mL of dichloromethane was added dropwise at 0° C. in inert atmosphere and with continuous stirring. Then, the mixture was stirred at room temperature for 24 h, and the solvent was distilled off under reduced pressure to give 8.46 g (37.4 mmol) of a white solid corresponding to the title compound. IR (KBr, cm$^{-1}$): 3380, 2650–2500, 1776.

Example 1

3-quinuclidyl N-benzyl-N-phenylcarbamate, hydrochloride

Method A

To a solution of 5.1 g (20 mmol) of ethyl N-benzyl-N-phenylcarbamate (Dannley, L. *J. Org. Chem.* 1957, 22, 268) and 7.63 g (60 mmol) of 3-quinuclidol in 120 mL of toluene, 800 mg (20 mmol) of sodium hydride (60% dispersion in oil) were added and the mixture was boiled for three hours. During this time toluene was to replace the distilled volume. The reaction crude was allowed to cool down, and was diluted with toluene (250 mL), washed with water and dried over anhydrous sodium sulphate. Then, the solvent was distilled off under reduced pressure. The obtained oil was treated at room temperature with hydrogen chloride saturated ethanol, the solvent was distilled off, and the obtained solid was broken up with a 1:1 ethyl acetate/diethyl ether mixture to give 230 mg (0.6 mmol) of a white solid corresponding to the title compound (m.p.: 54° C.).

Method B

To a suspension of 750 mg (2.58 mmol) of hydrochloride of 3-quinuclidyl chloroformate in 20 mL of 1,2-dichloroethane, a solution of 395 mg (2.15 mmol) of N-phenylbenzylamine in 5 mL of 1,2-dichloroethane was added dropwise. Once completed the addition, the mixture was refluxed for three hours. The reaction crude was allowed to cool down and the solvent distilled off under reduced pressure. The residue was purified by column chromatography (eluent: chloroform-methanol 10:1) yielding 720 mg (1.95 mmol) of a hygroscopic foam corresponding to the title compound. IR (KBr, cm$^{-1}$): 3400–3200, 2700–2300, 1700 cm$^{-1}$. $^1$H-RMN ($\delta_{TMS}$, CDCl$_3$, ppm): 12.30 (1H, s), 7.20–6.90 (10H, m), 5.10 (1H, m), 4.83 (2H, m), 3.52 (1H, m), 3.18 (4H, m), 2.80 (1H, m), 2.34 (1H, s), 1.92 (2H, m), 1.60 (2H, m).

Example 2

(R)-3-quinuclidyl N-benzyl-N-phenylcarbamate, hydrochloride

The title compound was obtained following the process described in Example 1 (Method A) starting with 390 mg (1.5 mmol) of ethyl N-benzyl-N-phenylcarbamate, 587 mg (4.6 mmol) of (R)-3-quinuclidol, and 61 mg (1.5 mmol) of sodium hydride. The obtained residue was purified by chromatographic column (eluent: chloroform:methanol 5:1), the isolated oil was treated at room temperature with hydrogen chloride saturated ethanol, and the solvent was distilled off. Then, the obtained solid was broken up with diethyl ether and dried under reduced pressure at 40° C. to give 310 mg (0.8 mmol) of a white solid corresponding to the title hydrochloride. m.p.: 50° C. $[\alpha]^{25}_D$: −26.5 (c=1.0, H$_2$O). IR (KBr, cm$^{-1}$): 2700–2300, 1700. $^1$H-RMN ($\delta_{TMS}$, CDCl$_3$, ppm): 12.30 (1H, s), 7.20–6.90 (10H, m), 5.10 (1H, m), 4.83 (2H, m), 3.50 (1H, m), 3.18 (4H, m), 2.80 (1H, m), 2.35 (1H, s), 1.99 (2H, m), 1.61 (2H, m).

Example 3

(R)-3-(N-benzyl-N-phenylcarbamoyloxy)-1-methylquinuclidinium iodide

A solution of 300 mg (0.89 mmol) of N-benzyl-N-phenylcarbamate of (R)-3-quinuclidyl (Example 2) and 60

µL of methyl iodide (0.98 mmol) in 9 mL of acetone was refluxed for 2 h. The reaction crude was allowed to cool down at room temperature and the solvent was distilled off under reduced pressure. The obtained solid was broken off with diethyl ether and dried at vacuum at 40° C. to give 480 mg (0.89 mmol) of a hygroscopic white solid corresponding to the title compound. IR (film, cm$^{-1}$): 1690.

Example 4

N-phenyl-N-benzyl-3-quinuclidyl carbamate, N-oxide

A suspension of 300 mg (0.9 mmol) of N-phenyl-N-benzyl-3-quinuclidyl carbamate in 20 mL of dichloromethane, and 95 mg (1.1 mmol) of sodium bicarbonate was cooled down at 0° C., and then 567 mg (1.1 mmol) of m-chloroperoxybenzoic acid (70%) were added. The reaction mixture was allowed to reach room temperature while stirring for one hour. Then, the organic layer was washed with a 5% solution of sodium thiosulphate, dried over anhydrous sodium sulphate, and filtered, and the solvent was distilled off under reduced pressure. The obtained residue was purified by chromatographic column using chloroform:methanol 5:1 as eluent. 289 mg (0.82 mmol) of a colouriess oil corresponding to the title compound were obtained. IR (film, cm$^{-1}$): 1702.

The following table includes other examples that have been prepared in a analogous way to the previous examples, as can be understood by any person skilled in the art. The values of the human $M_3$ antagonist activity (expressed as the binding affinity constant, $K_i$ (nM)) are shown in the $M_3$ column. The ratio between $M_2$ and $M_3$ receptor affinities is shown in the $M_2/M_3$ column, where a value greater than 1 indicates selectivity for the $M_3$ receptor.

| Ex. | M3 | M2/M3 | IR(cm$^{-1}$) |
| --- | --- | --- | --- |
| OXYBUTININ | 1.29 | 14 | — |
| TOLTERODINE | 47.5 | 1 | — |
| DARIFENACIN | 2.23 | 28 | — |
| YM-905 | 1.72 | 24 | — |

-continued

| Ex. | | M3 | M2/M3 | IR(cm$^{-1}$) |
|---|---|---|---|---|
| 1 | (structure) | 0.45 | 10 | 1700.0 |
| 2 | (structure) | 0.31 | 5 | 1700.0 |
| 3 | (structure) | 2.6 | 7 | 1690.9 |
| 4 | (structure) | — | — | 1702.3 |
| 5 | (structure) | 0.047 | 47 | 1706.1 |
| 6 | (structure) | 0.21 | 87 | 1704.1 |

-continued
| Ex. | | M3 | M2/M3 | IR(cm⁻¹) |
|---|---|---|---|---|
| 7 | 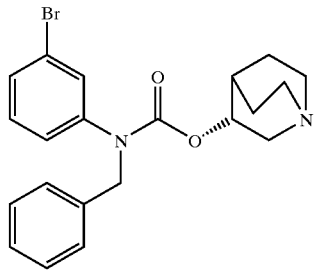 | 2.05 | 19 | — |
| 8 | 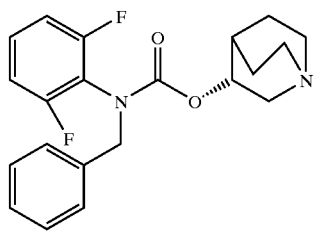 | 0.2 | 11 | 1712.7 |
| 9 | 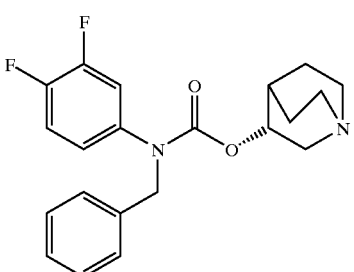 | 19.6 | 9 | 1713.6 |
| 10 | 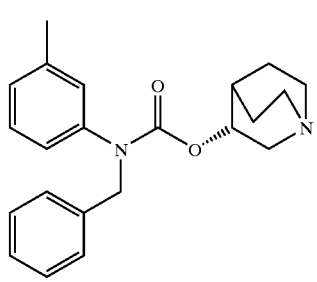 | 0.14 | 44 | 1693.8 |
| 11 | 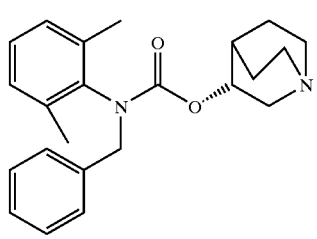 | 6.12 | 11 | 1697.7 |

-continued

| Ex. | | M3 | M2/M3 | IR(cm$^{-1}$) |
|---|---|---|---|---|
| 12 | (2,3-dihydro-1H-inden-5-yl)(benzyl)carbamate of quinuclidin-3-ol | 30.7 | 6 | 1687.9 |
| 13 | (4-cyanophenyl)(benzyl)carbamate of quinuclidin-3-ol | 4.31 | 17 | 2229.8 |
| 14 | (2-hydroxyphenyl)(benzyl)carbamate of quinuclidin-3-ol | 0.31 | 21 | 3460.5 |
| 15 | (2-fluoro-5-methylphenyl)(2-fluorobenzyl)carbamate of quinuclidin-3-ol | 0.53 | 21 | 1702.2 |
| 16 | phenyl(2-bromobenzyl)carbamate of quinuclidin-3-ol | 4.23 | 13 | 1712.0 |
| 17 | (3-fluorophenyl)(3-fluorobenzyl)carbamate of quinuclidin-3-ol | 0.054 | 196 | 1704.1 |

| Ex. | | M3 | M2/M3 | IR(cm⁻¹) |
|---|---|---|---|---|
| 18 | [structure: N-(2,3-difluorophenyl)-N-(4-fluorobenzyl)carbamate of quinuclidin-3-ol] | 0.92 | 154 | — |
| 19 | [structure: N-(2-fluoro-5-methylphenyl)-N-(4-chlorobenzyl)carbamate of quinuclidin-3-ol] | 1.2 | 23 | 1707.6 |
| 20 | [structure: N-(3-chlorophenyl)-N-(2,3-difluorobenzyl)carbamate of quinuclidin-3-ol] | 0.33 | 149 | 1706.1 |
| 21 | [structure: N-(2,4-difluorophenyl)-N-(2,4-dichlorobenzyl)carbamate of quinuclidin-3-ol] | 104.5 | 5 | 1714.0 |
| 22 | [structure: N-(3-methylphenyl)-N-(2,4-difluorobenzyl)carbamate of quinuclidin-3-ol] | 0.51 | 21 | 1700.0 |

-continued
| Ex. | | M3 | M2/M3 | IR(cm⁻¹) |
|---|---|---|---|---|
| 23 | 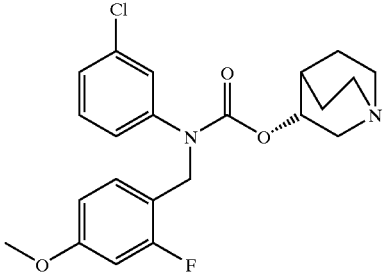 | 0.73 | 118 | 1694.1 |
| 24 | 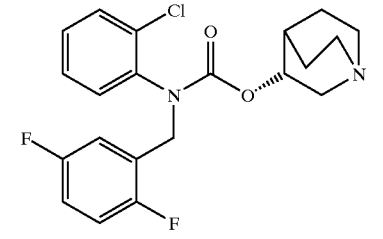 | 0.48 | 33 | 1707.9 |
| 25 | 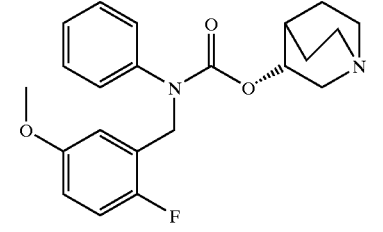 | 1.7 | 19 | 1693.6 |
| 26 | 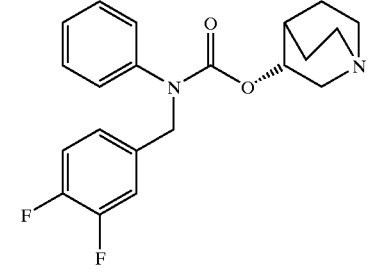 | 0.1 | 50 | 1697.8 |
| 27 | 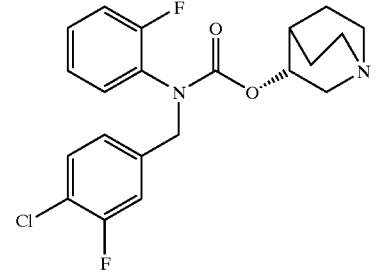 | 0.37 | 92 | 1704.1 |

-continued

| Ex. | | M3 | M2/M3 | IR(cm⁻¹) |
|---|---|---|---|---|
| 28 | (structure) | 1.5 | 35 | 1693.6 |
| 29 | (structure) | 1.4 | 50 | 1715.3 |
| 30 | (structure) | 0.09 | 74 | 1694.1 |
| 31 | (structure) | 0.32 | 52 | 1698.2 |
| 32 | (structure) | 3.3 | 19 | — |

-continued

| Ex. | | M3 | M2/M3 | IR(cm$^{-1}$) |
|---|---|---|---|---|
| 33 | (3-chlorophenyl)-N-(2,3,4-trifluorobenzyl) carbamate of (R)-quinuclidin-3-ol | 0.4 | 142 | 1701.3 |
| 34 | (3-methylphenyl)-N-(2,3,5-trifluorobenzyl) carbamate of (R)-quinuclidin-3-ol | 0.3 | 90 | 1693.5 |
| 35 | (3-methylphenyl)-N-(2,4,5-trifluorobenzyl) carbamate of (R)-quinuclidin-3-ol | 0.031 | 839 | 1699.7 |
| 36 | (3-fluorophenyl)-N-(3,4,5-trifluorobenzyl) carbamate of (R)-quinuclidin-3-ol | 0.04 | 545 | 1698.0 |
| 37 | (3,4-difluorophenyl)-N-(3,4,5-trifluorobenzyl) carbamate of (R)-quinuclidin-3-ol | 0.66 | 134 | 1703.8 |

-continued

| Ex. | | M3 | M2/M3 | IR(cm⁻¹) |
|---|---|---|---|---|
| 38 | | 0.23 | 40 | 1702.5 |
| 39 | | 0.32 | 84 | 1701.8 |
| 40 | | 0.066 | 92 | 1700.3 |
| 41 | | 0.11 | 271 | 1701.9 |
| 42 | | 1.17 | 38 | 1697.7<br>3360.0 |
| 43 | | 0.9 | 31 | 1698.2<br>2226.0 |

-continued
| Ex. | | M3 | M2/M3 | IR(cm$^{-1}$) |
|---|---|---|---|---|
| 44 | 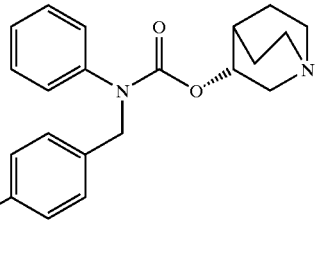 | 7.7 | 6 | — |
| 45 | 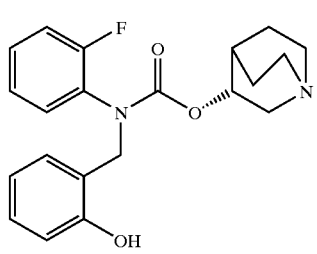 | 0.18 | 37 | 1706.2 3000–3400 |
| 46 | 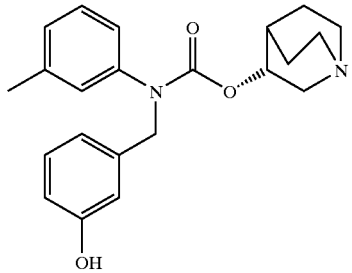 | 0.15 | 33 | 1693.8 3420 |
| 47 | 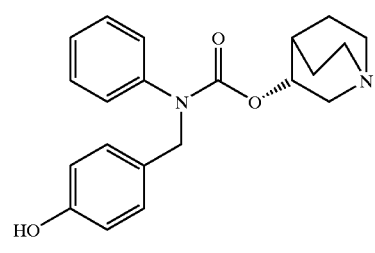 | 5.7 | 33 | 1692.6 3270.3 |
| 48 | 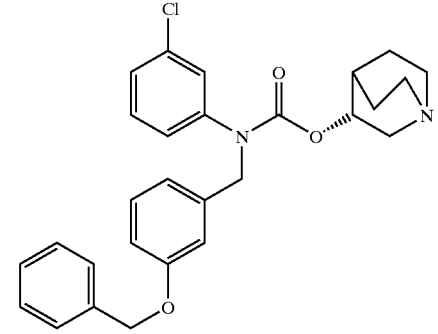 | 0.43 | 24 | 1704.1 |

-continued
| Ex. | | M3 | M2/M3 | IR(cm⁻¹) |
|---|---|---|---|---|
| 49 | 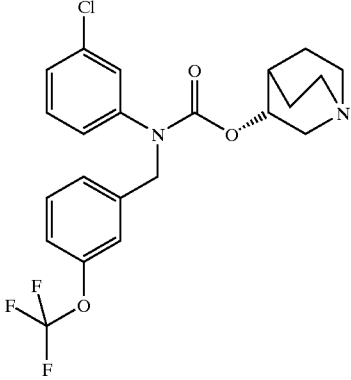 | 10.1 | 7 | 1701.5 |
| 50 | 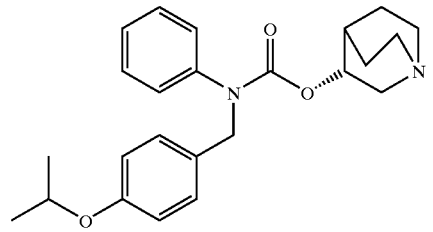 | 0.84 | 26 | 1698.0 |
| 51 | 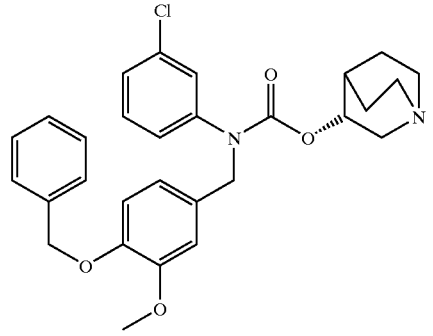 | 51.9 | 3 | — |
| 52 | 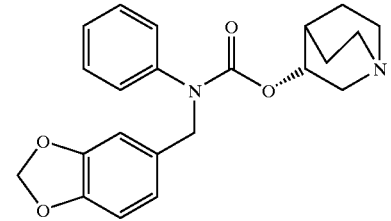 | 1.2 | 25 | 1708.4 |
| 53 | 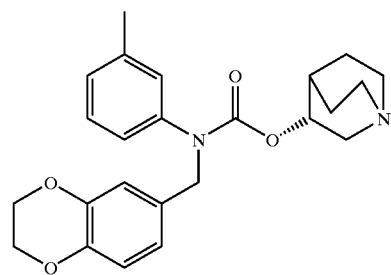 | 1.25 | 26 | 1701.7 |

-continued

| Ex. | | M3 | M2/M3 | IR(cm$^{-1}$) |
|---|---|---|---|---|
| 54 | (structure) | 0.6 | 32 | 1696.0 |
| 55 | (structure) | 0.35 | 110 | 1698.6 |
| 56 | (structure) | 0.75 | 37 | 1693.6 |
| 57 | (structure) | 0.025 | 300 | 1705.1 |
| 58 | (structure) | 0.088 | 93 | 1704.1 |
| 59 | (structure) | 0.77 | 90 | — |

-continued

| Ex. | | M3 | M2/M3 | IR(cm⁻¹) |
|---|---|---|---|---|
| 60 | (2-fluorophenyl, cyclohexenylmethyl carbamate quinuclidinyl ester) | 0.02 | 48 | 1710.6 |
| 61 | (3-chlorophenyl, cyclohexenylmethyl carbamate quinuclidinyl ester) | 0.35 | 74 | 1704.5 |
| 62 | (3-fluorophenyl, norbornylmethyl carbamate quinuclidinyl ester) | 0.22 | 115 | 1707.6 |
| 63 | (phenyl, norbornenylmethyl carbamate quinuclidinyl ester) | 0.06 | 64 | 1696.3 |
| 64 | (phenyl, 4-fluorobenzyl carbamate N-methyl quinuclidinium iodide) | 3.6 | 30 | — |
| 65 | (2-methylphenyl, benzyl carbamate N-methyl quinuclidinium iodide) | 14.3 | 13 | 1694.0 |

| Ex. | | M3 | M2/M3 | IR(cm⁻¹) |
|---|---|---|---|---|
| 66 | | 4.7 | 18 | 1702.5 |
| 67 | | 3.8 | 19 | 1698.1 |
| 68 | | 9.9 | 5 | 1706.9 |
| 69 | | 14.1 | 8 | 1715.5 |

What is claimed is:

1. A compound of formula (I)

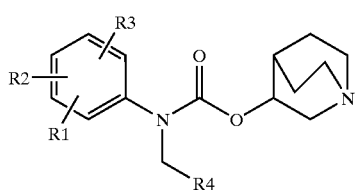

wherein R1, R2 and R3 are the same or different radicals, attached to the benzenic ring at any of their possible positions, and they are selected from the group consisting of H, OH, SH, CN, F, Cl, Br, I, ($C_1$–$C_4$)-alkylthio, ($C_1$–$C_4$)-alkoxyl, ($C_1$–$C_4$)-alkoxyl substituted with one or several F, carbamoylamine, ($C_1$–$C_4$)-alkyl and ($C_1$–$C_4$)-alkyl substituted with one or several F or OH; alternatively, either R1 and R2, or R2 and R3 may be forming a biradical selected from the group consisting of —$CH_2$—$CH_2$—$CH_2$— and —$CH_2$—$CH_2$—$CH_2$—$CH_2$—; and R4 is a radical selected from the group consisting of cyclopropyl, cyclobutyl, cyclopentyl, cyclohexyl, cyclohexenyl, norbornenyl, bicyclo[2.2.1]heptanyl, 2-, 3-, 4-pyridyl, 1-, 2-naphtyl, 1-, 2-benzodioxolanyl, 1-, 2-benzodioxanyl and phenyl substituted with one or several substituents selected from the group consisting of OH, SH, CN, F, Cl, Br, I, carbanioylamine, hydroxycarbonyl, $(C_1-C_4)$-alkoxycarbonyl, $(C_1-C_4)$-alkylthio, $(C_1-C_4)$-alkyl, $(C_1-C_4)$-alkoxyl, $(C_1-C_4)$-alkyl substituted with one or several F or OH, and $(C_1-C_4)$-alkoxyl substituted with one or several F;

or a pharmaceutically acceptable $(C_1-C_4)$-alkylamonium salt over the quinuclidyl nitrogen thereof, or a N-oxide over the quinuclidyl nitrogen thereof; or a stereoisomer, a stereoisomer mixture, a pharmaceutically acceptable salt, or a pharmaceutically acceptable solvate thereof.

2. A compound according to claim 1, wherein R4 is phenyl substituted with one or several substituents independently selected from the group consisting of: OH, SH, CN, F, Cl, Br, I, carbamoylamine, hydroxycarbonyl, $(C_1-C_4)$-alkoxycarbonyl, $(C_1-C_4)$-alkylthio, $(C_1-C_4)$-alkyl, $(C_1-C_4)$-alkoxyl, $(C_1-C_4)$-alkyl substituted with one or several F or OH, and $(C_1-C_4)$-alkoxyl substituted with one or several F.

3. A compound according to claim 1, wherein R4 is selected from the group consisting of cyclopropyl, cyclobutyl, cyclopentyl, cyclohexyl, cyclohexenyl, norbornenyl, bicyclo[2.2.1]heptanyl, 2-, 3-, 4-pyridyl, 1-, 2-naphthyl, 1-, 2-benzodioxolanyl, and 1-, 2-benzodioxanyl.

4. A compound according to claim 1, wherein the nitrogen of the quinuclidine ring is forming a pharmaceutically acceptable $(C_1-C_4)$-alkylamonium salt.

5. A compound according to claim 1, wherein the nitrogen of the quinuclidine ring is forming a N-oxide.

6. A compound according to claim 1 wherein the stereocenter corresponding to the 3 position in the quinuclidine ring is (R), having the formula:

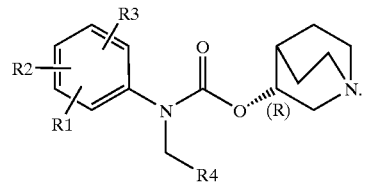

7. A method of treating urinary incontinence in a subject comprising administering to the subject in need thereof a therapeutic amount of a compound according to claim 1.

8. The method according to claim 7, wherein urinary incontinence is caused by unstable bladder.

9. A method of treating irritable bowel syndrome in a subject comprising administering to the subject in need thereof a therapeutic amount of a compound according to claim 1.

10. A method of treating a respiratory disease selected from chronic obstructive pulnionary disease, chronic bronchitis, asthma, emphysema, and rhinitis in a subject comprising administering to the subject in need thereof a therapeutic amount of a compound according to claim 1.

* * * * *